(12) United States Patent
Schultz et al.

(10) Patent No.: US 6,346,232 B1
(45) Date of Patent: *Feb. 12, 2002

(54) METHOD OF FORMING CONDUCTIVE LINES

(75) Inventors: Robert K. Schultz, Shoreview; David W. Schultz, Falcon Heights, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/537,151

(22) Filed: Mar. 29, 2000

Related U.S. Application Data

(63) Continuation of application No. 09/110,800, filed on Jul. 6, 1998, now abandoned, which is a continuation of application No. 08/455,872, filed on May 31, 1995, now Pat. No. 5,776,432, which is a continuation of application No. 07/769,547, filed on Oct. 1, 1991, now abandoned, which is a continuation-in-part of application No. 07/599,694, filed on Oct. 18, 1990, now abandoned.

(51) Int. Cl.$^7$ .................................................. A61K 9/12
(52) U.S. Cl. .......................................... 424/45; 424/46
(58) Field of Search ..................................... 424/45, 46

(56) References Cited

U.S. PATENT DOCUMENTS

| | | | |
|---|---|---|---|
| 2,868,691 A | 1/1959 | Porush et al. ................. | 167/54 |
| 2,885,427 A | 5/1959 | Ruh ........................ | 260/653.7 |
| 3,014,844 A | 12/1961 | Thiel et al. .................... | 167/82 |
| 3,320,125 A | 5/1967 | Grim ........................... | 167/54 |
| 3,897,779 A | 8/1975 | Hansen ....................... | 128/266 |
| 4,083,954 A | 4/1978 | Tsuchiya et al. .............. | 424/47 |
| 4,174,295 A | 11/1979 | Bargigia ..................... | 252/305 |
| 4,243,548 A | 1/1981 | Heeb et al. .................. | 252/305 |
| 4,352,789 A | 10/1982 | Thiel ........................... | 424/46 |
| 4,810,488 A | 3/1989 | Jinks ............................ | 424/45 |
| 4,851,211 A | 7/1989 | Adjei et al. .................... | 424/40 |
| 4,913,892 A | 4/1990 | Page et al. .................... | 424/45 |
| 5,118,494 A | 6/1992 | Schultz et al. ................ | 424/45 |
| 5,202,110 A | 4/1993 | Dalby et al. ................... | 424/45 |
| 5,225,183 A | 7/1993 | Purewal et al. ............... | 424/45 |
| 5,290,539 A | 3/1994 | Marecki ....................... | 424/45 |
| 5,345,980 A | 9/1994 | Burt et al. ...................... | 141/3 |
| 5,439,670 A | 8/1995 | Purewal et al. ............... | 424/45 |
| 5,474,759 A | 12/1995 | Fassberg et al. ............. | 424/45 |
| 5,605,674 A | 2/1997 | Purewal et al. ............... | 424/45 |
| 5,674,471 A | * 10/1997 | Akehurst et al. ............. | 424/45 |
| 5,674,473 A | 10/1997 | Purewal et al. ............... | 424/45 |
| 5,681,545 A | 10/1997 | Purewal et al. ............... | 424/45 |
| 5,683,677 A | 11/1997 | Purewal et al. ............... | 424/45 |
| 5,695,743 A | 12/1997 | Purewal et al. ............... | 424/45 |
| 5,720,940 A | 2/1998 | Purewal et al. ............... | 424/45 |
| 5,766,573 A | 6/1998 | Purewal et al. ............... | 424/45 |
| 5,776,432 A | 7/1998 | Schultz et al. ................ | 424/45 |
| 5,776,434 A | 7/1998 | Purewal et al. ............... | 424/45 |
| 6,006,745 A | 12/1999 | Marecki ............... | 128/200.23 |

FOREIGN PATENT DOCUMENTS

| | | |
|---|---|---|
| DE | 3905726 | 8/1990 |
| EP | 172672 | 1/1988 |
| EP | 0372777 | 6/1990 |
| EP | 0384371 | 8/1990 |
| EP | 504112 | 9/1992 |
| EP | 616525 | 9/1995 |
| GB | 2001334 A | 1/1979 |
| JP | H2-200627 | 8/1990 |
| WO | 86/04233 | 7/1986 |
| WO | 91/11173 | 8/1991 |
| WO | 91/11495 | 8/1991 |
| WO | 91/11496 | 8/1991 |
| WO | 92/22287 | 12/1992 |
| WO | 93/04671 | 9/1993 |

OTHER PUBLICATIONS

Taisho Yakuhin Kogyo, demand for trail against Japanese patent 2769925, Aug. 28, 2000 (Osaka, Japan).

Osaka Association Hospital Pharmacists, Edited, Completely Revised *Iyakuhin Youran*, Yakugyou Jihou Co., Ltd, published Oct. 5, 1986, cover, explanatory notes, p. 292, and back flap.

Written Statement of Austen John Woolfe of Norton Health Care, dated Aug. 17, 2000.

Robinson, Joseph R., and Lee, Vincent H.L., "Influence of Drug Properties and Routes of Drug Administration of the Design of Sustained and Controlled Release Systems," *Controlled Drug Delivery, Fundamentals and Applications,* chapter 1, pp. 3–4 and 45–47 (Mercel Dekker, Inc., New York, 1987).

Certified copy of the Test Report of the Medicines Testing Laboratory dated Aug. 3, 1999, "Report of the Results of the Twelve Month Time Point for Beclomethasone Dipropionate Inhalers Stability Study".

Certified copy of Study Protocol Agreement for Analysis of Chemical Stability of BDP HFA MDI between Norton (Waterford) Ltd. and Medicines Testing Laboratory.

*Nihon Yakkyoku Hou Kaisetsusho* AΩBΩCΩDΩEΩF, 10$^{th}$ Revised Edition, first published Jul. 25, 1981, inside cover flap, table of contents, pp. A–29, A–36, and inside flap of back cover (Hirokawa Shoten Co., Ltd., Japan).

Test report dated Aug. 17, 2000, compiled by Hideko Shigefuji of Taisho Yakuhin Kogyo). Particle sizes are measured for Beclazone 50 Inhaler (of Taisho Yakuhin) and Becotide 50 Inhaler (of Nippon Glaxo).

Campos, et al, "Beclomethasone Dipropionate in the Treatment of corticosteroid–dependent Bronchial Asthma. Comparative Study of Two Aerosol Preparations", *Pharmatherapeutica*, vol. 1, No. 3, 1977, pp. 552–556.

(List continued on next page.)

*Primary Examiner*—Raj Bawa
(74) *Attorney, Agent, or Firm*—Ted K. Ringsred; MarySusan Howard; Robert W. Sprague

(57) ABSTRACT

Pharmaceutical solution aerosol formulations comprising beclomethasone 17,21 dipropionate, ethanol, and a propellant selected from the group consisting of 1,1,1,2-tetrafluoroethane, 1,1,1,2,3,3,3-heptafluoropropane, and a mixture thereof.

7 Claims, No Drawings

OTHER PUBLICATIONS

Taisho "Reply" dated Aug. 29, 2000, In 3M v. Taisho Yakuhin Kogyo, Case No. 12 (Wa) 7221, Osaka, Japan.

Taisho "Brief 1" with exhibits B–2–B9, dated Oct. 6, 2000, in 3M v. Taisho Yakuhin Kogyo, Case No. 12 (Wa) 7221, Osaka, Japan.

Taisho "Preparatory Document (2)" with exhibits B10–B18, dated Jan. 22, 2001, 3M v. Tashio Yakuhin Kogyo, Case No. 12 (Wa) 7221, Osaka, Japan.

Taisho "Preparatory Document (3)" with exhibits B19–B22, dated Apr. 9, 2001, 3M v. Taisho Yakuhin Kogyo, Case No. 12, (Wa) 7221, Osaka, Japan.

Taisho "Description of Exhibits (4)," dated Feb. 8, 2001, 3M v. Taisho Yakuhin Kogyo, Case No. 12 (Wa) 7221, Osaka, Japan.

IVAX, et al. v. Minnesota Mining and Manufacturing Company, Complaint filed Aug. 30, 2000, Civil Action 00–3219, U.S. District Court for the Southern District of Florida.

ICI News Release, "ICI Announces 'Ozone Friendly' Production Plants", dated Nov. 22, 1988 (ICI Amernicas Inc., Willmington, Delaware).

Compos, et al. "Beclomethasone Dipropionate in the Treatment of Corticoteroid–Dependent Bronchial Asthma. Comparative Study of Two Aerosol Preparations", *Pharmatherapeutica*, vol. 1, No. 3, 1977, pp. 552–556.

3M v. Taisho Yakuhin Kogyo, Translation of Reply filed by Taisho in response to Complaint by 3M for infringement of Japanese patent 2769925, Aug. 31, 2000 (Osaka 12 (Wa) 7221).

Du Pont, "Fluorocarbon Azeotropes", *Research Disclosure*, vol. 162 p. 70, #16265 (1977).

Gennaro, *Remington's Pharmaceutical Sciences*, p. 962 (Mack Publishing Company, Inc., 1985).

Dalby, R.N. and Byron P.R., "Comparison of Output Particle Size Distributions from Pressurised Aerosols Formulated as Solutions or Suspensions", *Pharmaceutical Res.*, vol. 5, No. 1 p. 36 (1988).

Sciarra, J., in Lachman, Lieberman & Kanig, *The Theory and Practice of Industrial Pharmacy*, 2nd Edition, pp. 270 and 276–280 (Lea & Febiger, Philadelphia, 1976).

Ranucci, J., "Pharmaceutical Aerosol Technology, Aerosol Formulation Development", The Institute for Applied Pharmaceutical Sciences, May 21–23, p.1–122 (1990).

Sciarra, J., in Lachman, Lieberman & Kanig, *The Theory & Practice of Industrial Pharmacy*, 3rd Ed., pp. 589–618 (Lea & Febiger, 1986).

Backstrom, K., et al., "Measurements of Droplet Size Distributions from Metered Dose Inhalers with Different Vapour Pressures and Contents of Surfactant", *J. Aerosol Science*, vol.19, No. 7, pp. 1097–1100 (1988).

Thoma, K., AEROSOLE—Moglichkeiten und Probleme einer Darreichungsform, Werbe– und Vertriebsgesellschaft Dt. Apotheker mbH Frankfurt, p. 153–161 (1970).

Oradell N.J., *Physicians' Desk Reference*, PDR 40 Edition, p. 1900 (Medical Economics Company Inc., 1986).

Dalby R.N., et al., "CFC Propellant Substitution: P–134a as a Potential Replacement for P–12 in MDI's", *Pharmaceutical Technology*, pp. 26–33, (Mar. 1990).

Oberholz, A., "Fur den Schutz des Lebens auf der Erde, Die schwierige Suche nach Alternativen zu den Fluorochlorkohlenwasserstoffen", *Frankfurter Allegemeine Zeitung*, p. 7 (Oct. 25, 1989).

Product brochure, "Hoechst zum Ersatz von FCKW", Hoechst Chemikalien, pp. 1–3, Sep. 1990 (Hoechst Aktiengesellschaft, Frankfurt, Germany).

Morck, H., "EG–Kommission: FCKW–Verbot 1997", *Pharmazeutische Zeitung*, Nr. 9, 135. Jahrgang, pp. 30–31 (Frankfurt, Germany, Mar. 1990).

Product information, "DIN–Sicherheitsdatenblatt der Hoechst AG vom betreffend FKW 227", (Hoechst Aktiengesellschaft, Germany, Jan. 1988).

*The Merck Index*, 11$^{th}$ Ed., p. 158–159 (Merck and Company, Inc., 1989).

Gunella G., Melica A., Fabbri M., Cavalli A., Schiavina M., "Effetti sulla funzione ventilatoria e surrenalica di un cortisonico a grossa molecola, il beclometasone dipropionato, soministrato per via inalatoria", *Minerva Pneumologica*14(1), pp. 34–45, 1975.

Gunella G., Melica A., Fabbri M., Cavalli A., Schiavina M., Galeri C., "Effetti sulla funzione ventilatoria e surrenalica di un cortisonico a grossa molecola, il beclometasone dipropionato, soministrator per via inalatoria", *Folia Allergol Immunol Clin*, XXI (5), pp. 360–375, 1974.

Oradel, N.J., *Physicians' Desk Reference*, PDR 39 Edition, 1985, Medicinal Economics Company Inc., pp. 1291–1293.

European Patent Office Opposition Division decision, dated Dec. 27, 1996, re European Patent EP–B–0 553 298 (3M).

Jacob, J., United Kingdom Patents Court decision, dated Jun. 30, 1997, in the High Court of Justice, Chancery Division, Patents Court, combined cases CH/96/3771 and CH/96/3773 (re European Patent No. 0,372,777, 0,499,344, and 0,553,298.

Expert Report of John Sciarra, dated Mar. 14, 1997, in the U.K. High Court of Justice, Chancery Division, Patents Court, before the Honorable Mr. Justice Jacob, combined cases CH/96/3771 and CH/96/3773 (re European Patent Nos. 0,372,777, 0,499,344, and 0,553,298).

Expert Report of Ian Smith, dated Mar. 17, 1997, in the U.K. High Court of Justice, Chancery Division, Patents Court, before the Honorable Mr. Justice Jacob, combined cases CH/96/3771 and CH/96/3773 (re European Patent No. 0,372,777, 0,499,344, and 0,553,298.

Extracts from the transcripts of the proceedings in the U.K. Patents Court, dated Jun. 4–10, 1997, in the High Court of Justice, Chancery Division, Patents Court, before the Honorable Mr. Justice Jacob, combined cases CH/96/3771 and CH/96/3773 (re European Patent No. 0,372,7772, 0,499, 344, and 0,553,298).

Extract from IPACT history, "A Case for Cooperation, The Story of IPACT–I and II", p. 4, submitted in the U.K. High Court of Justice, Chancery Division, Patents Court, before the Honorable Mr. Justice Jacob, combined cases CH/96/3771 and CH/96/3773 (re European Patent Nos. 0,372,777, 0,499,344, and 0,553,298).

L'Informatore Farmaceutico, *Italian Directory of Drugs and Manufacturers*, 38$^{th}$ edition, p. 142 (Clenil Spray), (Organizzione Editoriale Medico–Farmaceutica S.R.L., Milano, Italy, 1978).

Statement of Dr. Ian Smith, pp. 1–6, dated Nov. 2, 1998 in European Opposition Proceedings re EP 0553298 (Appeal Case No. T0153/97–332).

Moren, F., "Pressurized Aerosols for Inhalation", *International Journal of Pharmaceutics*, vol. 8, No. 1, Mar, 1981, pp. 1–4 (Elsevier/North–Holland Biomedical Press).

Moren, F., "Aerosol Dosage Forms and Formulations", *Aerosols in Medicine Principles, Diagnosis and Therapy*, Chapter 10, pp. 261–287, (Elsevier 1985).

Denoel, A., "Aerosols", *Galenic Pharmaceutics*, vol. IV, Chapter III, p. 153–168 (Liege University Press 1969).

Atkins, P., "the Design and Development of Inhalation Drug Delivery Systems", *Pharmaceutical Inhalation Aerosol Technology*, Chapter 6, p. 155–185, edited by A. Hickey (Marcel Dekker, Inc., New York 1992).

Aerosol Search through *Physician's Desk Reference* (PDR) (1991), submitted in European Opposition Proceedings re EP 0553298 (Appeal Case No. T0153/97–332).

Frank, Bruce H., letters to R.F. Browne dated Feb. 6, 1997 and Feb. 25, 1997 in European Opposition Proceedings re EP 0553298 (Appeal Case No. T0153/97–332) (with Nov. 2, 1998 cover letter from Urquart–Dykes & Lord).

Gennaro, A.R. (1985) *Remington's Pharmaceutical Science*, Mack Publishing Co., Easton, PA, 1672.

Ansel, H.C. et al, (1995), Pharmaceutical Dosage Forms and Drug Delivery Systems, Williams & Wilkins, pp. 450–453.

European Patent Office Technical Board of Appeals decision, dated Dec. 2, 1998, re European Patent EP–B–0 553 298 (3M).

\* cited by examiner

US 6,346,232 B1

METHOD OF FORMING CONDUCTIVE LINES

This is a continuation of application Ser. No. 09/110,800 filed Jul. 6, 1998, now abandoned, which is a continuation of application Ser. No. 08/455,872, filed May 31, 1995, now U.S. Pat. No. 5,776,432, which is a continuation of application Ser. No. 07/769,547, filed Oct. 1, 1991, now abandoned, which is a continuation-in-part of application Ser. No. 07/599,694, filed Oct. 18, 1990, now abandoned.

TECHNICAL FIELD OF THE INVENTION

This invention pertains to solution aerosol formulations suitable for use in administering drugs. In another aspect this invention pertains to formulations comprising beclomethasone 17,21 dipropionate.

BACKGROUND OF THE INVENTION

Pharmaceutical suspension aerosol formulations currently use a mixture of liquid chlorofluorocarbons as the propellant. Fluorotrichloromethane, dichlorodifluoromethane and dichlorotetrafluoroethane are the most commonly used propellants in aerosol formulations for administration by inhalation.

Chlorofluorocarbons have been implicated in the destruction of the ozone layer and their production is being phased out. Hydrofluorocarbon 134a (HFC-134a, 1,1,1,2-tetrafluoroethane) and hydrofluorocarbon 227 (HFC-227, 1,1,1,2,3,3,3-heptafluoropropane) are viewed as being less destructive to ozone than many chlorofluorocarbon propellants; furthermore, they have low toxicity and vapor pressure suitable for use in aerosols.

Beclomethasone 17,21 dipropionate is commercially available as an aerosol product comprising a suspension of a chlorofluorohydrocarbon solvate of beclomethasone 17,21 dipropionate in chlorofluorohydrocarbon propellants. Preparation of the solvate requires several processing steps and is required in order to obtain a stable aerosol formulation, i.e., one in which the micronized particles of active ingredient remain in the desired respirable particle size range. A solution formulation of beclomethasone 17,21 dipropionate could simplify formulation manufacture and increase the respirable fraction (i.e., the percentage of active ingredient able to reach the airways of the lung where the pharmaceutical effect is exerted).

U.S. Pat. No. 2,868,691 discloses a self-propelling pharmaceutical aerosol formulation comprising i) a medicament; ii) a propellant represented generally by the formula $C_mH_nCl_yF_z$, wherein m is an integer less than 3, n is an integer or zero, y is an integer or zero, and z is an integer, such that n+y+z=2m+2; and iii) a cosolvent which assists in the dissolution of the medicament in the propellant. Ethanol is an example of a cosolvent disclosed in this patent. The above formula representing the propellant component generically embraces HFC-134a. This patent does not, however, disclose beclomethasone 17,21 dipropionate or suggest how stable solution aerosol formulations (i.e., formulations that are chemically stable and exhibit desirable respirable fraction) containing any propellant and beclomethasone 17,21 dipropionate can be prepared.

SUMMARY OF THE INVENTION

The present invention provides an aerosol formulation comprising a therapeutically effective amount of beclomethasone 17,21 dipropionate, a propellant comprising a hydrofluorocarbon selected from the group consisting of 1,1,1,2-tetrafluoroethane, 1,1,1,2,3,3,3-heptafluoropropane, and a mixture thereof, and ethanol in an amount effective to solubilize the beclomethasone 17,21 dipropionate in the propellant, the formulation being further characterized in that substantially all of the beclomethasone 17,21 dipropionate is dissolved in the formulation, and the formulation is substantially free of any surfactant.

Certain of the preferred formulations of the invention exhibit very desirable chemical stability and provide respirable fractions significantly greater than commercially available beclomethasone 17,21 dipropionate products. Moreover, the formulations of the invention are convenient to manufacture since no solvate of the active ingredient need be prepared.

The pharmaceutical solution aerosol formulations of the invention are suitable for pulmonary, buccal, or nasal administration.

DETAILED DESCRIPTION OF THE INVENTION

All weight percentages recited herein are based on the total weight of the formulation unless otherwise indicated.

The medicament beclomethasone 17,21 dipropionate is generally present in a formulation of the invention in a therapeutically effective amount, i.e., an amount such that one or more metered volumes of the formulation contains an amount of drug effective to exert the intended therapeutic action. Preferably the medicament will constitute about 0.02 to about 0.6 percent by weight, more preferably about 0.05 to about 0.5 percent by weight of the total weight of the formulation.

Ethanol is generally present in an amount effective to solubilize the beclomethasone 17,21 dipropionate in the propellant. Preferably, ethanol constitutes about 1 to about 20 percent by weight of the total weight of the aerosol formulation. More preferably, ethanol constitutes about 2 to about 12 percent by weight and even more preferably about 2 to about 10 percent by weight of the aerosol formulation. Most preferably, ethanol will be present in an amount sufficient to dissolve substantially all of the medicament present in the formulation and to maintain the medicament dissolved over the time period and conditions experienced by commercial aerosol products, but not substantially in excess of said amount. Particularly desirable formulations of the invention, while not containing amounts of ethanol substantially in excess of that required (during manufacture of the formulation) to dissolve the amount of active ingredient employed, may be subjected to a temperature of −20° C. without precipitation of the active ingredient.

The hydrofluorocarbon propellant can be HFC-134a, HFC-227, or a mixture thereof. The propellant preferably constitutes from about 80 to about 99 percent by weight, preferably from about 88 to about 98 percent by weight, and more preferably about 90 to about 98 percent by weight of the total weight of the aerosol formulation. The hydrofluorocarbon propellant is preferably the only propellant present in the formulations of the invention. However, one or more other propellants (e.g., 1-chloro-1,1-difluoroethane) can also be present.

The formulations of the invention are substantially free of any surfactant. By "substantially free" as used in the instant specification and claims is meant that the formulations contain no more than 0.0005 percent by weight of a surfactant based on the total weight of the formulation. Preferred formulations contain no surfactant. Presence of a significant amount of a surfactant is believed to be undesirable in the case of solution formulations of beclomethasone 17,21 dipropionate because surfactants such as oleic acid and lecithin seem to promote chemical degradation of the active ingredient when the latter is dissolved in the mixture of HFC-134a and ethanol.

Preferred formulations according to the invention consist essentially of beclomethasone 17,21 dipropionate in an amount of about 0.05 to about 0.35 percent by weight based on the weight of the total formulation, ethanol in an amount of about 2 to about 8 percent by weight based on the total weight of the formulation, and 1,1,1,2-tetrafluoroethane.

The solution formulations of the invention can be prepared by dissolving the desired amount of beclomethasone 17,21 dipropionate in the desired amount of anhydrous ethanol accompanied by stirring or sonication. The aerosol vial may then be filled using conventional cold-fill or pressure-fill methods.

The following examples are provided to illustrate the invention but should not be construed as limiting the invention.

EXAMPLES 1–7

Formulations containing the following ingredients (TABLE I) in the indicated amounts were prepared with the percentages being expressed in parts by weight based upon the total weight of the particular formulation. The active ingredient employed in preparing the formulations of Examples 2, 3, and 5–7 was beclomethasone dipropionate, USP while that employed in preparing the formulations of Examples 1 and 4 was a conventional trichloromonofluoromethane solvate of beclomethasone dipropionate. The formulations of Examples 1, 4, 5 and 6 were prepared by i) dissolving the active ingredient in the ethanol; ii) metering the solution obtained above into an aluminum vial and crimping a continuous valve onto the vial; iii) pressure-filling the vial with 1,1,1,2-tetrafluoroethane; iv) chilling the vial to –60° C.; and v) replacing the continuous valve with a 50 microliter valve which is available under the trade designation "W303-98" from 3M. The formulations of Examples 2, 3 and 7 were prepared by i) dissolving the active ingredient in the ethanol; ii) metering the solution obtained above into an aluminum vial and crimping a 50 microliter pressure-fill valve which is available under the trade designation Spraymiser™ M3652 from 3M onto the vial; and iii) pressure-filling the vial with 1,1,1,2-tetrafluoroethane.

The actuator employed in the case of all the formulations was a solution actuator available under the trade designation "M3756" from 3M. The elastomer employed in the valves in the case of all formulations was that available under the trade designation "DB-218" from American Gasket and Rubber Co. (Chicago, Ill.)

TABLE I

| Ingredient | Example | | | | | | |
|---|---|---|---|---|---|---|---|
| | 1 | 2 | 3 | 4 | 5 | 6 | 7 |
| Beclomethasone 17, 21 Dipropionate | 0.1% | 0.1% | 0.25% | 0.3% | 0.4% | 0.44% | 0.5% |
| Ethanol (anhydrous) | 3% | 5% | 10% | 5% | 10% | 10% | 15% |
| 1,1,1,2-Tetrafluoroethane | 96.9% | 94.9% | 89.75% | 94.7% | 89.6% | 89.56% | 84.5% |

TABLE II

| Storage Time (Weeks) | 0 | 2 | 4 | 7 | 12 |
|---|---|---|---|---|---|
| % Recovery | 101.4, 98.7 | 101.9, 101.6 | 100.8, 99.6 | 99.3, 95.5 | 100.6 102.6 |

The formulation of Example 1 did not exhibit precipitation of the active ingredient on freezing to –60° C.

The respirable fraction provided by the formulations of Examples 1–7 was determined using an Anderson MK II Cascade Impactor with the average respirable fraction obtained from each being in excess of 40%. In the case of the formulations of Examples 1 and 4, the respirable fraction was about 76% and about 70%, respectively.

From the above data, it is believed that the optimum amount of active ingredient for low and high strength products would be about 0.08 and 0.34 percent by weight, respectively, based on the total weight of the formulations.

EXAMPLE 8

A mixture containing 1.67 g of beclomethasone 17,21 dipropionate and 160 g of cold (–65° C.) ethanol was homogenized using a Virtis 45 homogenizer. The resulting suspension was placed in a one gallon stainless steel filling vessel equipped with a stir bar. A 1839 g portion of cold (–65° C.) 1,1,1,2-tetrafluoroethane was added to the filling vessel. After about 5 minutes of stirring, a solution was obtained. The resulting formulation contained 0.08 percent by weight of beclomethasone 17,21 dipropionate, 8.0 percent by weight of ethanol and 91.92 percent by weight of 1,1,1,2-tetrafluoroethane. The formulation was cold filled into aerosol vials and then 50 μL cold fill valves were crimped onto the vials.

EXAMPLE 9

Using the general method of Example. 8, a formulation containing 0.34 percent by weight of beclomethasone 17,21 dipropionate, 8.0 percent by weight of ethanol and 91.66 percent by weight of 1,1,1,2-tetrafluoroethane was prepared. The formulation was cold filled as a suspension into aerosol vials which were then equipped with 50 μL cold fill valves. The formulation changed from a suspension to a solution as the vials warmed to room temperature.

EXAMPLE 10

A formulation containing 0.3 percent by weight of beclomethasone 17,21 dipropionate, 10 percent by weight of ethanol and 89.7 percent by weight of 1,1,1,2,3,3,3-heptafluoropropane was prepared by i) weighing a 30 mg portion of beclomethasone 17,21 dipropionate into an aerosol vial ii) crimping a continuous valve onto the vial and iii) pressure filling with a solution containing 10 percent ethanol in 1,1,1,2,3,3,3-heptafluoropropane.

What is claimed is:

1. A method of preparing a solution aerosol formulation comprising the step of combining a therapeutically effective amount of beclomethasone 17, 21 dipropionate, a propellant selected from the group consisting of 1,1,1,2-tetrafluoroethane, 1,1,1,2,3,3,3-heptafluoropropane, and a mixture thereof, and ethanol in an amount of 2 to 12 percent by weight to solubilize the beclomethasone 17, 21 dipropionate in the propellant.

2. The method of claim 1, wherein said formulation comprises 0.05 to 0.5% by weight beclomethasone 17, 21 dipropionate.

3. The method of claim 1, wherein said propellant is present in an amount of 88 to 98 percent by weight.

4. The method of claim 1, wherein said formulation comprises 1,1,1,2-tetrafluoroethane as the only propellant.

5. The method of claim 1, wherein said formulation comprises 1,1,1,2,3,3,3-heptafluoropropane as the only propellant.

6. The method of claim 1, wherein said formulation is free of surfactant.

7. The method of claim 1, wherein said formulation consists essentially of a therapeutically effective amount of beclomethasone 17, 21 dipropionate, a propellant selected from the group consisting of 1,1,1,2-tetrafluoroethane, 1,1,1,2,3,3,3-heptafluoropropane, and a mixture thereof, and an amount of ethanol 2 to 12 percent by weight to solubilize the beclomethasone 17, 21 dipropionate in the propellant.

* * * * *

UNITED STATES PATENT AND TRADEMARK OFFICE
CERTIFICATE OF CORRECTION

| | | |
|---|---|---|
| PATENT NO. | : 6,346,232 B1 | Page 1 of 1 |
| DATED | : February 12, 2002 | |
| INVENTOR(S) | : Robert K. Schultz and David W. Schultz | |

It is certified that error appears in the above-identified patent and that said Letters Patent is hereby corrected as shown below:

<u>Title page,</u>
Item [54], Title, please delete "METHOD OF FORMING CONDUCTIVE LINES" and insert in place thereof -- BECLOMETHASONE SOLUTION AEROSOL FORMULATIONS --.

<u>Column 4,</u>
Line 20, please insert before Table II the following paragraph:
-- The chemical stability of the formulation of Example 4 was determined in respect to recovery of the active ingredient over time when the formulation was stored at 40°C. Table II contains the data. --

Signed and Sealed this

Thirty-first Day of December, 2002

JAMES E. ROGAN
*Director of the United States Patent and Trademark Office*